United States Patent [19]

Clark et al.

[11] Patent Number: 5,158,096

[45] Date of Patent: Oct. 27, 1992

[54] ORTHOPEDIC MEASUREMENT DEVICE AND METHODOLOGY TO QUANTITATIVELY AND SIMULTANEOUSLY MEASURE DISTANCE AND FORCE DURING A PASSIVE STRETCHING OF THE MANDIBLE

[75] Inventors: Glenn T. Clark, Culver City; Martin E. Orro, Lake Elizabeth, both of Calif.

[73] Assignee: The Regents of the University of California, Oakland, Calif.

[21] Appl. No.: 686,075

[22] Filed: Apr. 16, 1991

[51] Int. Cl.$^5$ .............................................. A61B 5/103
[52] U.S. Cl. ...................................... 128/777; 33/514; 433/69; 433/72; 73/380
[58] Field of Search .............. 128/774, 777, 776, 25 R; 272/94, 95; 433/27, 68, 69, 71, 140, 72; 73/379, 380, 381; 33/512, 513, 514

[56] References Cited

U.S. PATENT DOCUMENTS

| | | | |
|---|---|---|---|
| 2,182,390 | 1/1937 | Reardon | 433/140 |
| 3,813,096 | 5/1974 | Welch | 272/95 |
| 4,014,097 | 3/1977 | Pameijer | 433/27 |
| 4,127,112 | 11/1978 | Sherlock et al. | 128/774 |
| 4,447,207 | 5/1984 | Kataoka et al. | 433/69 |
| 4,592,727 | 6/1986 | Bloomfield | 433/71 |
| 4,687,003 | 8/1987 | Burckhardt | 128/777 |
| 4,700,695 | 10/1987 | Davis et al. | 128/25 R |
| 4,718,850 | 1/1988 | Knebelman | 433/72 |
| 4,834,112 | 5/1989 | Machek et al. | 128/777 |
| 4,883,046 | 11/1989 | Fontenot | 128/25 R |
| 4,909,502 | 3/1990 | Beeuwkes, III et al. | 272/95 |
| 4,938,230 | 7/1990 | Machek et al. | 128/777 |
| 4,943,047 | 7/1990 | Noble | 272/68 |
| 4,955,367 | 9/1990 | Homsy | 128/25 R |
| 4,997,368 | 3/1991 | Mayer et al. | 433/72 |

Primary Examiner—Max Hindenburg
Assistant Examiner—Guy V. Tucker
Attorney, Agent, or Firm—Daniel L. Dawes

[57] ABSTRACT

Simultaneous measurement of a border position of a mandible joint opening and the "end-feel" force required to achieve the border position are effectuated through a single apparatus which applies a force to the upper and lower jaw of a patient and continuously measures the degree of opening of the jaw as the mandible joint opens. When a predetermined amount of force is achieved as measured by either a detected degree of spring compression within the device or release of a detent mechanism, the force is automatically or manually withdrawn leaving an indicator showing the maximum jaw opening. Simultaneous border position and "end-feel" force can also be measured in alternative embodiment through reverse scissors and a mechanical dial and slider for continuously measuring the degree of opening while an electrical transducer measures the force applied until the "end-feel" force has been achieved as digitally read out.

21 Claims, 2 Drawing Sheets

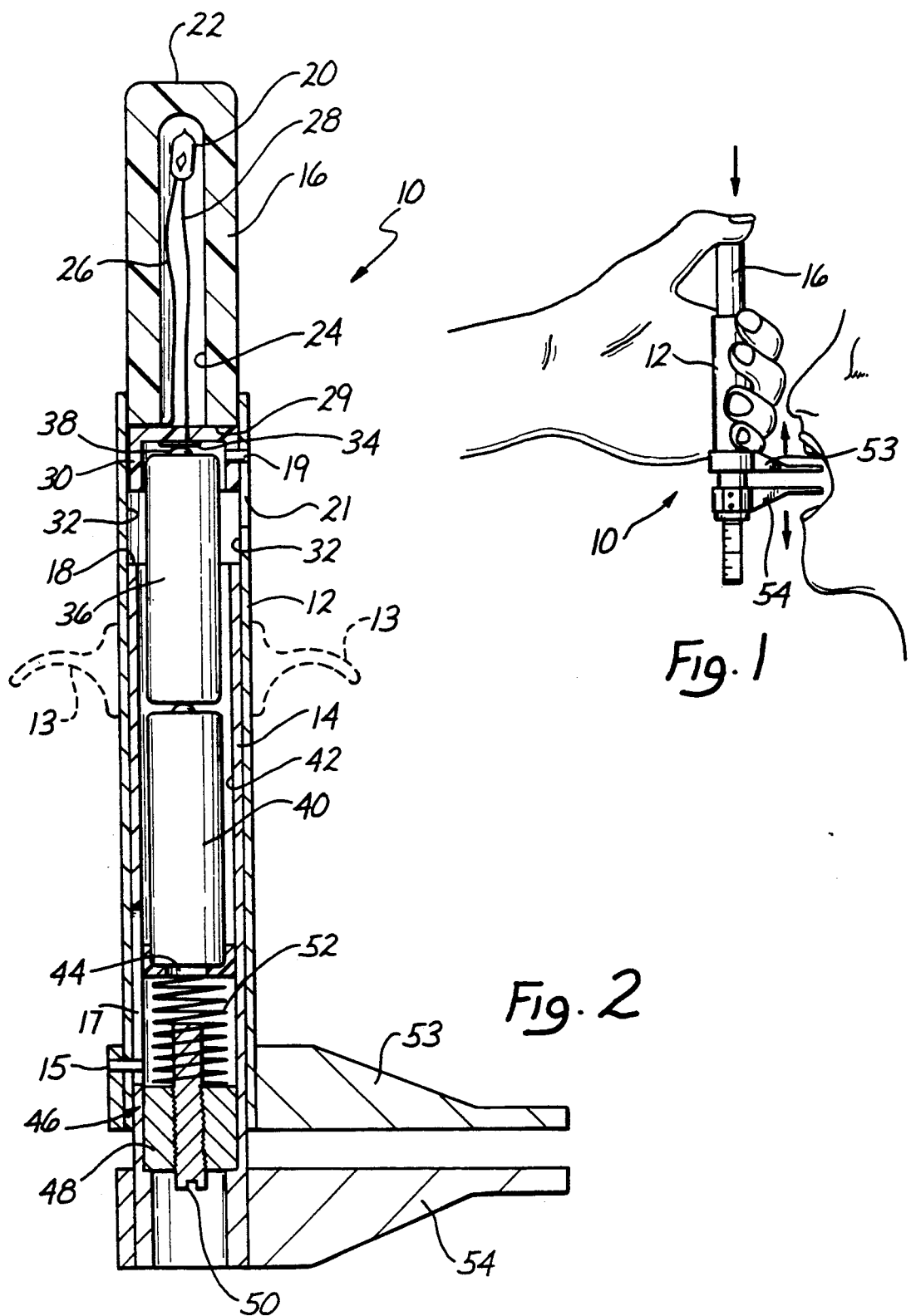

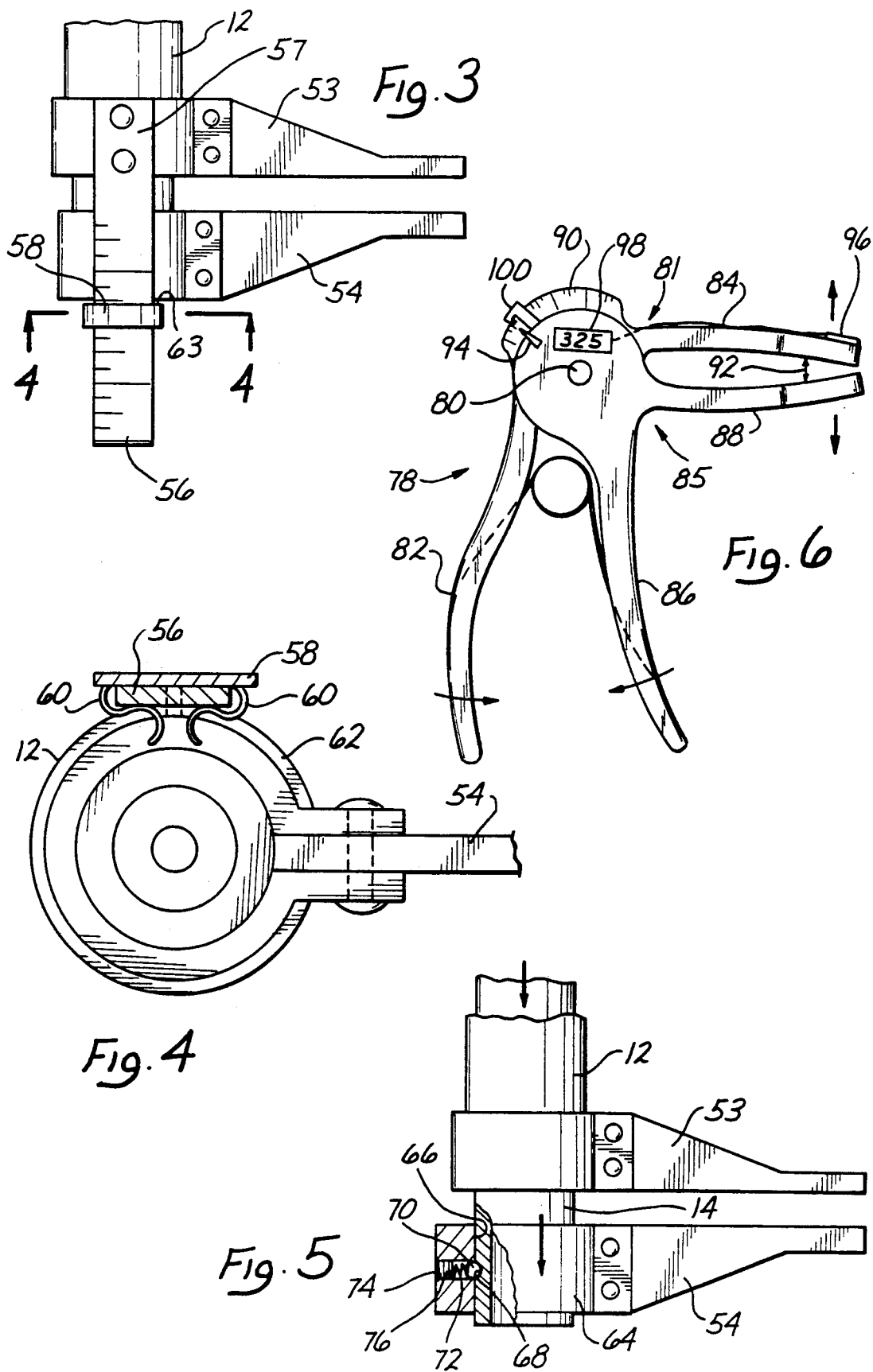

ORTHOPEDIC MEASUREMENT DEVICE AND METHODOLOGY TO QUANTITATIVELY AND SIMULTANEOUSLY MEASURE DISTANCE AND FORCE DURING A PASSIVE STRETCHING OF THE MANDIBLE

BACKGROUND OF THE INVENTION

1. Field of the Invention

The invention relates to the field of orthopedic devices and in particular to devices for measurement of mandibular function.

2. Description of the Prior Art

TMJ examinations are routinely done both diagnostically as well as to measure therapeutic outcome of treatment. In temporomandibular joint (TMJ) examinations the patient is asked to open his or her mouth as wide as possible to provide an indicator of mandibular function. Measurement of the opening is used diagnostically to determine a number of different diseases or dysfunctions of the temporomandibular joint.

Many different types of apparatus and methods have been devised to measure the opening or movement of the double joint mandible. Electro-optical systems have been shown by Kataoka et.al., "Mandibular Motion Diagnostic Device," U.S. Pat. No. 4,447,207 (1984); and electromechanical systems are described by Burckhardt, "Dental Device," U.S. Pat. No. 4,687,003 (1987) and Pameijer, "Method and Apparatus for Measuring and Recording Three Dimensional Condylermovements of the Mandible," U.S. Pat. No. 4,014,097 (1977). However, all of these systems only measure distances or positions and none are capable of a simultaneous force measurement. Still further they are complex, expensive and ill adapted to general clinical practice.

Devices are also known which apply a force to the jaw for therapeutic purposes, but have no capability of quantifying the force applied or simultaneously correlating a distance with it. See, Beeuwkes, III et.al., "Passive Jaw Exerciser," U.S. Pat. No. 4,909,502 (1990) and Fontenot, "Involuntary Oscillator System for the Mandible," U.S. Pat. No. 4,883,046 (1989) sold as the Transjaw by Transjaw Company of Houston, Tex.

The distance of jaw opening is defined as the active stretch distance. Typically, the doctor inserts his thumb and index finger into the patient's mouth between the upper and lower jaws to stretch the jaws apart as far as possible. The physician assesses both the distance, termed the border position, and the "end-feel", the amount of force required to achieve the border position. Through long and repeated experience, the physician develops by trial and error a sense for the "end-feel", and therefore assesses temporomandibular joint dysfunction based upon the rigidity, softness and other characteristics of the feel of the jaw opening when it reaches its end point. Similar manual application of force to a transducer mounted the patient's teeth and physician's thumb to measure the end force, and the use of light sensitive cells in combination with a recording oscilloscope to measure the border position is shown by J. Hesse et. al., "*Craniomandibular Stiffness Toward Maximum Mouth Opening in Healthy Subjects: A Clinical and Experimental Investigation,*" Journal of Craniomandibular Disorders: Facial & Oral Pain, Vol. 4, No. 4, page 257-65 (1990). This technique is impractical as a clinical tool because the equipment is relatively sophisticated, largely not portable, expensive and not commonly available in a dentist's office.

As a matter of clinical practice border postion and end point feel are empirically determined by feel. In some cases the border position is determined by joint dysfunction or in other cases the border position may be limited by muscular dysfunction, each having a different end field. Only the border position is quantitative, when measured by a ruler or measuring rule, and the detection of the "end-feel" is entirely qualitative. Clinical diagnosis is imprecise using this prior art technique and can be developed only through long periods of experience by trial and error, in other words physician must develop an educated feel for the pair of parameters, force and distance, associated with mandible opening. While devices for simultaneously measuring force and correlated body movement, comprising the movement of multiple numbers of joints, are known, see Farrar, Jr., "Orthopedic Muscle Testing Apparatus," U.S. Pat. No. 3,922,918 (1975), no practical clinical device is known which simultaneously measures border position and end feel in the temporomandibular joint.

Therefore, what is needed is some type of means whereby force and distance of a mandible opening can be accurately, quickly and simultaneously made in a practical clinical setting.

BRIEF SUMMARY OF THE INVENTION

The invention is a clinical apparatus for simultaneous measurement of "endfeel" force and mandible joint opening of an upper and lower jaw of a patient. The apparatus comprises a first element for forcing a mandible joint opening. A second element records the maximum interdental distance of the forced mandible joint opening. A third element simultaneously measures the force applied to the mandible joint of the patient when the maximal interdental distance has been achieved. As a result, "end-feel" force and mandible joint opening is simultaneously and quantitatively measured.

The first element for forcing the mandible joint opening comprises a lower jaw piece for contacting the lower jaw of the mandible joint of the patient, and an upper jaw piece for contacting the upper jaw of the mandible joint of the patient. The lower jaw piece and upper jaw piece each are connected to a body for disposing the upper and lower jaw pieces in opposite directions to force the mandible joint opening.

The body comprises an upper tube having the upper jaw piece connected thereto and a lower cylinder assembly. The lower cylinder assembly is adapted to telescopically slide relative to the upper tube. The lower jaw piece is connected to the lower cylinder assembly. The upper tube is arranged and configured to allow it to be grasped. The lower cylinder assembly extends from and is exposed beyond an upper end of the upper tube. The upper end of the lower cylinder assembly is arranged and configured to provide a surface for the application of longitudinal downward manual force on the lower cylinder assembly to force the mandible joint opening.

The upper tube and lower cylinder assembly are arranged and configured to allow grasping of the upper tube with the fingers of one hand and the forcing of the lower cylinder assembly downward by the thumb of the same hand.

In another embodiment the upper tube further comprises a finger bracket in the style of a syringe for allowing disposition of the upper tube between the fingers of one hand and retention of the upper tube within the hand by juxtaposition of the fingers of the hand under the finger bracket.

The lower cylinder assembly is comprised of a lower tube, and a forcing element. The forcing element is telescopically disposed within the lower tube. The lower tube is connected to the lower jaw piece. The forcing element applies force through the lower jaw piece to the mandible joint opening until a predetermined amount of force is applied as indicated by the forcing element.

The forcing element comprises a rod assembly telescopically disposed through the upper tube for transmitting manual pressure applied to the rod to the lower jaw piece. A spring is provided to require the predetermined amount of force to be applied through the rod to the lower jaw piece to force the mandible joint opening. An indicator indicates when the predetermined amount of force has been applied through the rod and spring element to the lower jaw piece.

The rod assembly and spring are telescopically disposed within the lower tube. The spring is disposed on one end of the lower tube and an opposing end of the spring is in contact with the rod assembly. The indicator comprises an electrode extending through the spring to contact the rod assembly. The rod assembly further comprises at least one battery having a terminal. The terminal of the battery is disposed toward the electrode and makes contact with the electrode when the spring has been compressed by a predetermined extent corresponding to the predetermined force. The rod assembly further comprises a circuit for indicating when the terminal of the battery contacts the electrode.

The circuit comprises the at least one battery, a light source, the electrode, and an element for electrically coupling the light source to the battery and to the electrode to complete the circuit when the terminal of the battery contacts the electrode.

The light source is a light-emitting diode disposed in an upper end of the rod assembly. At least a portion of the rod assembly is at least translucent to allow visual observation of operation of the light-emitting diode.

The electrode is coupled to the lower tube and is adjusted to adjust the degree of compression of the spring and thus the predetermined corresponding force.

In an alternative embodiment the first element is a pair of reverse scissors. The second element for recording distance comprises a pointer fixed to one of the reverse scissors, an angle plate connected to the other one of the pair of reverse scissors, and a slider which is slidingly disposed on the angle plate and arranged and configured to contact the pointer. The pointer moves the slider along the angle plate to the position of maximum opening of the reverse scissors. The third element for simultaneously measuring force of the mandible joint opening comprises a force transducer mounted on one of the reverse scissors for contact with the mandible joint of the patient and a circuit for recording maximal force applied to the transducer.

In still another embodiment the third element for simultaneously measuring the force applied to the mandible joint opening comprises a release element for automatically releasing the first element from the mandible joint so that force is no longer applied to the mandible joint when a predetermined magnitude of force has been applied to the mandible joint. The first element for forcing the mandible joint opening comprises a lower jaw piece for contacting the lower jaw of the mandible joint of the patient, an upper jaw piece for contacting the upper jaw of the mandible joint of the patient, and a body. The lower jaw piece and upper jaw piece are each connected to the body and are disposed in opposite directions to force the mandible joint opening. The release element comprises a detent assembly for coupling the lower jaw piece to the body. The detent assembly is arranged and configured to decouple the lower jaw piece when the predetermined force has been applied.

The invention is also characterized as a method for quantitatively and simultaneously measuring "end-feel" force and border position of a mandible joint opening of a patient comprising the steps of disposing an apparatus within the mandible joint opening of the patient. The mandible joint opening is forced apart with a predetermined magnitude of force. The maximum extension of the apparatus within the mandible joint opening is continuously measured. A determination is made when the predetermined force has been achieved, so that the continuous measurement of the mandible joint opening provides the border position and the predetermined force is selected at or above the "end-feel" force.

The invention and its embodiments can be visualized in the following drawings wherein like elements are referenced by like numerals.

BRIEF DESCRIPTION OF THE DRAWINGS

FIG. 1 is a simplified side view of a first embodiment showing its use with a patient.

FIG. 2 is a side-sectional view of a first embodiment of the invention.

FIG. 3 is a side view of a measurement ruler combined as part of the device of FIG. 2.

FIG. 4 is an end view of the end of the device depicted in FIG. 2 as seen through lines 4—4 of FIG. 3.

FIG. 5 is a cross-sectional view of the lower jaw piece of a second embodiment of the invention.

FIG. 6 is a plan side view of a third embodiment of the invention.

The invention and its various embodiments can be better understood by now turning to the following detailed description.

DETAILED DESCRIPTION OF PREFERRED EMBODIMENTS

Simultaneous measurement was a border position of a mandible joint opening and the "end-feel" force required to achieve the border position is effectuated through a single apparatus which applies a force to the upper and lower jaw of a patient and continuously measures the degree of opening of the jaw as the mandible joint opens. When a predetermined amount of force is achieved as measured by either a detected degree of spring compression within the device or release of a detent mechanism, the force is automatically or manually withdrawn leaving an indicator showing the maximum jaw opening. Simultaneous border position and "end-feel" force can also be measured in alternative embodiment through reverse scissors and a mechanical dial and slider for continuously measuring the degree of opening while an electrical transducer measures the force applied until the "end-feel" force has been achieved as digitally read out, or by any means of torque or force sensing such as by release mechanisms described below.

The orthopedic measurement device of the invention as shown in FIG. 1 applies a maximum force to the mandible at a predetermined or preset magnitude, which can be adjusted by the user of the device. The magnitude of force is preferably just at or above the end feel magnitude. The device is comprised of a body incorporating the mechanism for presetting the preset force of mandibular opening, and a pair of jaw pieces extending from the body for insertion into the mouth against the upper and lower teeth to stretch the jaw to the border position. The jaw pieces of the device are spread apart thereby opening the patient's mandible until the preset force is achieved. When this occurs, a light in the device or other signaling device is illuminated and the force released. A measurement ruler fixed at the side of the device includes a sliding cursor, which is moved as the jaw pieces of the device open the patient's mandible. In one embodiment when the maximum force is reached, as indicated by the light or other indicator, the physician will allow the jaw pieces of the device to be forced back toward each other in response to the resistance of the patient's mandible. However, the sliding cursor on the measurement ruler will remain at the maximum opening of the mandible or at the border position. Thus, it can be quantitatively determined that the mandible was opened by a quantified degree, as indicated by the sliding cursor on the ruler, when the predetermined force was simultaneously realized.

In the illustrated embodiment shown in FIGS. 2-4 the force is directly and manually applied through a tube and cylinder combination or through a reverse scissors. It is to be expressly understood that the scope of the invention is sufficient to include other means for the application of force to the jaw, such as mechanical ratcheting devices driven by a squeeze-grip handle, pneumatic systems utilizing pumped cylinder or bladders, electromechanically driven mechanisms, electromagnetic solenoids and any means now known or later developed for generating an increasing amount of force. Two embodiments are shown as preferred, but should not be read as limiting the invention defined in the claims.

In another embodiment shown in FIG. 5 one of the jaw pieces of the device is designed so as to release when a predetermined and maximum force is obtained as opposed to activating some type of electro-optical or electromechanical indicator.

In still another embodiment of the invention shown in FIG. 6, the device is formed in the shape of reversed scissors, that is having two handgrips, which when brought towards each other, cause the jaw pieces of the device to spread apart. The opening of the jaw pieces of the device is indicated by a mechanical pointer gauge, again with a sliding cursor, and the force is simultaneously measured through a force transducer.

The invention has also been described as providing a predetermined endforce, which may vary from one patient to another. However, it is also expressly contemplated that conventional electronics may be incorporated which also provides a predetermined time rate of increase of force. It is anticipated that a device with this type of capacity will have application as a research tool.

Turn now to FIG. 2 where orthopedic measuring-device 10 is depicted in side cross-sectional view. The body of the device is comprised of a first metallic tube 12 in which a second metallic tube 14 is telescopically and slidingly disposed. Relative extension of tubes 12 and 14 is limited by a pin and slot combination, pin 15 being perpendicularly fixed into tube 12 and extending therefrom, and slot 17 being longitudinally defined in tube 14. Also slidingly disposed or disposable in first tube 12 is a clear or translucent plastic rod 16 which is set adjacent end 18 of the second tube 14. Rod 16 is fixed by adhesive or other means to cap 30 which is slidable in tube 12. Rod 16 and cap 30 are retained in tube 12 by a pin 19 and slot 21 combination. As discussed below this allows rod 16 to continue downward in tube 12 to compress spring 52 when jaw piece 54 and tube 14 attached thereto have been stopped by the patient's border position. Enough length is provided in slot 21 to allow spring 52 to be compressed enough to allow contact between terminal 44 of battery 40 and adjusting screw 50 without impingement of pin 19 against slot 21.

Rod 16 has a light source 20 disposed in its end, preferable near the uppermost end 22. Light 20 may be imbedded within rod 16 as an integral casting or disposed therein in an axial bore 24. In any case, electrical leads 26 and 28 to light 20 are extended along the length of tube 16 to its lower end 29. Lower end 29 of rod 16 is provided with a insulative cup 30 which is arranged and configured to receive the end of a standard battery. In the illustrated embodiment a AA size battery 36 is electrically coupled to contact 34. Cup 30 is disposed in tube 12 so that it makes sliding electrical contact with the inside surface 32 of first tube 12. Wire 26 is sliding electrically coupled to tube 12. The other wire of the pair of wires extended from light 20, wire 28, is insulatively disposed through the center of cup 30 and coupled to an electrical terminal 34 inside cup 30.

The first battery 36 is disposed into cup 30 and has one of its terminal ends 38 disposed against terminal 34 within cup 30. A second battery 40 also slip fits within interior bore 42 of second tube 14 and is placed end to end with first battery 36. Batteries 36 and 40 form a series circuit with terminal end 44 of battery 40 being exposed as a normally open contact.

The lower end 46 of second tube 14 is fitted with a plug 48 through which an adjusting screw 50 is axially disposed. A compression spring 52 of a known or calibrated spring constant is disposed on top of plug 48 and has its opposing end bearing against the terminal end of battery 40 but not making electrical contact with terminal tip 44. A washer or retainer cup may be place over the lower end of second battery 40 between battery 40 and spring 52 if desired.

An upper jaw piece 53 is fixed to first tube 12 while a lower jaw piece 54 is fixed to plug 48 or alternatively to second tube 14. Jaw pieces 53 and 54 are arranged and configured to mount or contact mandibles of the patient through contact with the teeth or gums.

The physician can therefore with one hand grasp upper tube 12 and with the thumb of that same hand press down on end 22 of rod 16 forcing lower jaw piece 54 away from upper jaw piece 53. In doing so, lower end of battery 40 compresses spring 52 bringing terminal 44 toward adjustment screw 50. Ultimately when a predetermined amount of compression of spring 52 has been achieved, terminal 44 will contact screw 50 thereby completing the electrical circuit and lighting light source 20. At the moment light source 20 lights, the compression of spring 52 is known and hence the force which is urging upper jaw piece 53 away from lower jaw piece 54 similarly known to be the same.

In an alternative embodiment a syringe like grip 13 as shown in dotted outline in FIG. 2 may be used to provide another mode of gripping and applying force to rod 16.

As shown in FIGS. 3 and 4, device 10 is provided with a measuring rule 56 disposed on its outside surface. One end 57 of rule 56 is fixed relative to upper jaw piece 53 or tube 12. In the illustrated embodiment rule 56 is screwed or riveted to a circular housing which fits upper jaw piece 53 to tube 12.

Rule 56 extends downwardly past lower jaw piece 54 and has a sliding cursor 58 resiliently, but slidingly engaging rule 56. As best seen in the end view of FIG. 4, sliding cursor 58 is slidingly attached to rule 56 by means of a pair of resiliently clasping springs 60. Therefore, when jaw pieces 53 and 54 are spread apart with a force sufficient to compress spring 52 to cause light source 20 to be illuminated, cursor 58 will simultaneously have been slid by virtue of the juxtaposition of retainer springs 60 against the bottom end 62 of jaw piece 54 or its fitting connecting it to tube 14 to a maximum point of extension, that is the border position. The border position is read directly from rule 56 by means of the juxtaposition of edge 63 of cursor 58 against rule 56. Therefore, even though the physician will quickly release the maximum pressure extending jaw pieces 53 and 54 apart, cursor 58 will remain in its maximum extended position by means of its resilient frictional engagement with rule 56.

It is to be expressly understood that the force indicator as shown in the embodiments of FIGS. 1–4 is shown only by way of example and not by way of limitation. For example, it is expressly contemplated that light source 20 is a light emitting diode although an incandescent or low voltage neon bulb may be submitted. It is also contemplated that a sound indicator could be used instead of or with a light indicator. It is also contemplated that a force transducer and force gauge could be used directly. For example, instead of spring 52 a force transducer could be placed within second tube 14 and a rigid plunger for applying a force from second tube 14 to plug 48 substituted for batteries 36 and 40. Appropriate electronics would be included within device 10 together with a digital readout meter for the amount of force applied to the transducer, which by virtue of the position of the transducer, would also be the force applied to separate lower jaw piece 54 from upper jaw piece 53.

FIG. 5 illustrates another embodiment of the invention wherein lower jaw piece 54 is fixed to second tube 14 by means of a detent mechanism. Instead of being rigidly fixed to tube 14, fitting 64 of lower jaw piece 54 slides onto tube 14 which extends into fitting 64 through a bore 66 in fitting 64. Tube 14 has a cavity 68 defined in one side into which a detent ball 70 is forced by detent spring 72. The pressure of detent spring 72 forcing detent ball into indentation 68 is determined according to an adjustment screw 74 which is threaded into bore 76 in which spring 72 and ball 70 are disposed.

When a predetermined amount of maximum force is applied by the mandibular joint to lower jaw piece 54, fitting 64 will be snapped from its engagement with tube 14 and slide upwardly. Again, this disengagement will automatically occur whenever the predetermined force is exceeded. The amount of force can be varied or set according to the compression of spring 72 and threaded adjustment screw 74. Measurement of the border position is determined as before by a sliding rule such as described in connection with the embodiment of FIGS. 1–4.

Yet another embodiment is depicted in FIG. 6 by a reverse scissors generally denoted by reference numeral 78. Reverse scissors 78 is comprised of two pieces pivotally coupled together at pivot 80. A first piece 81 has a handle portion 82 and an upper jaw piece portion 84. The second piece 85 has a handle portion 86 and a lower jaw piece portion 88. As handle portions 82 and 86 are drawn together, jaw pieces 84 and 88 separate. First piece 81 has a gauge plate 90 attached and centered about pivot 80. Gauge plate 90 is marked with gradations directly calibrated to correspond to the linear opening 92 of jaw pieces 84 and 88. Second piece 85 has a pointer 94 attached thereto which will indicate on gauge plate 90 the degree of rotation of jaw pieces 84 and 88 and hence the magnitude of separation 92.

A strain gauge 96 is mounted on the upper surface of jaw piece 84, for example, and is coupled through conventional microelectronics (not shown) to a digital readout meter 98. The amount of force by which jaw piece 88 is thus downwardly forced against the patient's mandible is directly measured by digital readout meter 98 at the same time border position is measured by distance 92. To facilitate this, a sliding cursor 100 similar in construction to cursor 58 is frictionally engaged with gauge plate 90 and can be driven by pointer 94 along the edge of gauge plate 90 to the point of maximum extension. Similarly, the digital readout meter 98 may be electronically programmed either to remain at the maximum readout or to activate a sound or light alarm when a predetermined force has been achieved as sensed by transducer 96.

Many modifications and alterations may be made by those having ordinary skill in the art without departing from the spirit and scope of the invention. For example, where a rate of increase of force is desired, the output of the transducer can be fed back to a microprocessor packaged with the apparatus which will sample the force, store it over time, calculate a time rate of change or derivative of the force, and display the calculated result. Such calculated rates of change of force may be combined with programmable means for applying the force at a predetermined rate or time profile. The means for applying the force is digitally controlled in a closed loop feedback with the transducer and the calculated rate of change of force. Therefore, it must be understood that the invention as defined by the following claims which are to include not only the literal scope of the claims, but encompasses all equivalents for performing substantially the same function in substantially the same way to obtain substantially the same result.

We claim:

1. A clinical apparatus for simultaneous indication of "end-feel" force and measurement of mandible joint opening of an upper and lower jaw of a patient, said "end-feel" force being a predetermined magnitude of force beyond which further opening of said mandible joint becomes substantially limited, comprising:

means for forcing a mandible joint open;
means for recording the maximum interdental distance of said forced mandible joint opening when said "end-feel" force has been achieved; and
means for simultaneously and repeatably indicating the application of said "end-feel" force applied to said mandible joint of said patient when said maximal interdental distance has been achieved,
whereby "end-feel" force and mandible joint opening is simultaneously and quantitatively measured.

2. The apparatus of claim 1 wherein said means for forcing said mandible joint open comprises:
   a lower jaw piece for contacting said lower jaw of said mandible joint of said patient;
   an upper jaw piece for contacting said upper jaw of said mandible joint of said patient; and
   a body, said lower jaw piece and upper jaw piece each connected to said body for disposing said upper and lower jaw pieces in opposite directions to force said mandible joint opening.

3. The apparatus of claim 1 wherein said means for simultaneously and repeatedly indicating the application of said "end-feel" force applied to applied to said mandible joint comprises release means for automatically releasing said means from said mandible joint so that force is no longer applied to said mandible joint when a predetermined magnitude of force has been applied to said mandible joint.

4. The apparatus of claim 3 wherein said means for forcing said mandible joint open comprises a lower jaw piece for contacting said lower jaw of said mandible joint of said patient, an upper jaw piece for contacting said upper jaw of said mandible joint of said patient, and a body, said lower jaw piece and upper jaw piece each connected to said body for disposing said upper and lower jaw pieces in opposite directions to force said mandible joint opening,
   wherein said release means comprises a detent assembly for coupling said lower jaw piece to said body, said detent assembly arranged and configured to decouple said lower jaw piece when said predetermined force has been applied.

5. A clinical apparatus for simultaneous indication of "end-feel" force and measurement of mandible joint opening of an upper and lower jaw of a patient, said "end-feel" force being a predetermined magnitude of force beyond which further opening of said mandible joint becomes substantially limited, comprising:
   means for forcing a mandible joint open;
   means for recording the maximum interdental distance of said forced mandible joint opening when said "end-feel" force has been achieved; and
   means for simultaneously and repeatedly indicating the application of said "end-feel" force applied to said mandible joint of said patient when said maximal interdental distance has been achieved,
   wherein said means for forcing said mandible joint open comprises:
   a lower jaw piece for contacting said lower jaw of said mandible joint of said patient;
   an upper jaw piece for contacting said upper jaw of said mandible joint of said patient; and
   a body, said lower jaw piece and upper jaw piece each connected to said body for disposing said upper and lower jaw pieces in opposite directions to force said mandible joint opening,
   wherein said body comprises an upper tube having said upper jaw piece connected thereto and a lower cylinder assembly, said lower cylinder assembly adapted to telescopically slide relative to said upper tube, said lower jaw piece being connected to said lower cylinder assembly, said upper tube being arranged and configured to allow grasping thereof, said lower cylinder assembly extending from and exposed beyond an upper end of said upper tube, said upper end of said lower cylinder assembly arranged and configured to provide a pressure surface for manually forcing said lower cylinder assembly longitudinally downward to force said mandible joint opening,
   whereby "end-feel" force and mandible joint opening is simultaneously and quantitatively measured.

6. The apparatus of claim 5 wherein said upper tube and lower cylinder assembly are arranged and configured to allow grasping of said upper tube with the fingers of one hand and the forcing of said lower cylinder assembly downward by the thumb of said same hand.

7. The apparatus of claim 5 wherein said upper tube further comprises a finger bracket in the style of a syringe for allowing disposition of said upper tube between the fingers of one hand and retention of said upper tube within said hand by juxtaposition of said fingers of said hand under said finger bracket.

8. The apparatus of claim 7 wherein said upper tube and lower cylinder assembly are arranged and configured to allow grasping of said upper tube with the fingers of one hand and the forcing of said lower cylinder downward by the thumb of said same hand.

9. The apparatus of claim 5 wherein said lower cylinder assembly is comprised of:
   a lower tube; and
   a forcing means telescopically disposed within said lower tube, said lower tube being connected to said lower jaw piece, said forcing means for applying a force through said lower jaw piece to said mandible joint opening until a predetermined amount of force is applied as indicated by said forcing means.

10. The apparatus of claim 9 wherein said forcing means comprises:
    a rod assembly telescopically disposed through said upper tube for transmitting manual pressure applied to said rod to said lower jaw piece;
    spring means for requiring said predetermined amount of force to be applied through said rod to said lower jaw piece to force said mandible joint opening; and
    indicator means for indicating when said predetermined amount of force has been applied through said rod and spring means to said lower jaw piece.

11. The apparatus of claim 10 wherein said rod assembly and spring means are telescopically disposed within said lower tube, said spring means being disposed on one end of said lower tube and an opposing end of said spring means being in contact with said rod assembly, said indicator means comprising a electrode extending through said spring means to contact said rod assembly, said rod assembly further comprising at least one battery having a terminal, said terminal of said battery disposed toward said electrode and making contact with said electrode when said spring means has been compressed by a predetermined extent corresponding to said predetermined force, said rod assembly further comprising a circuit for indicating when said terminal of said battery contacts said electrode.

12. The apparatus of claim 11 wherein said circuit comprises said at least one battery, a light source, said electrode, and means for electrically coupling said light source to said at least one battery and to said electrode to complete said circuit when said terminal of said battery contacts said electrode.

13. The apparatus of claim 12 wherein said light source is a light-emitting diode disposed in an upper end of said rod assembly, at least a portion of said rod assembly being at least translucent to allow visual observation of operation of said light-emitting diode.

14. The apparatus of claim 11 wherein said electrode is coupled to said lower tube and is adjusted to adjust said degree of compression of said spring means and thus said predetermined corresponding force.

15. A clinical apparatus for simultaneous indication of "end-feel" force and measurement of mandible joint opening of an upper and lower jaw of a patient, said "end-feel" force being a predetermined magnitude of force beyond which further opening of said mandible joint becomes substantially limited, comprising;
   means for forcing a mandible joint open;
   means for recording the maximum interdental distance of said forced mandible joint opening when said "end-feel" force has been achieved; and
   means for simultaneously and repeatedly indicating the application of said "end-feel" force applied to said mandible joint of said patient when said maximal interdental distance has been achieved,
   wherein said means for forcing said mandible joint open is a pair of reverse scissors, a reverse scissor being defined as a pair of curved arms coupled together at a pivot point, said curved arms having a grip portion, said coupled curved arms together so that movement of said grip portions of said arms towards each other causes the remaining and opposing ends of said curved arms to move away from each other, and wherein said means for recording distance comprises a pointer fixed to one of said curved arms, an angle plate connected to said other one of said pair of curved arms, and a slider being slidingly disposed on said angle plate and arranged and configured to contact said pointer, said pointer moving said slider along said angle plate to the position of maximum opening of said reverse scissors,
   whereby "end-feel" force and mandible joint opening is simultaneously and quantitatively measured.

16. The apparatus of claim 15 wherein said means for simultaneously and repeatedly indicating the application of said "end-feel" force applied to said mandible joint comprises a force transducer mounted on one of said curved arms for contact with said mandible joint of said patient and a circuit for recording maximal force applied to said transducer.

17. A method for quantitatively and simultaneously measuring "end-feel" force and border position of a mandible joint opening of a patient to obtain repeatably accurate measurements of said border position of said mandible joint, said border position being defined as that extent of opening of said mandible joint beyond which the application of additional opening force fails to produce a substantially greater opening, said "end-feel" force being defined as that predetermined magnitude of force beyond which further opening of said mandible joint becomes substantially limited, comprising the steps of:
   disposing an apparatus within said mandible joint opening of said patient;
   forcing said mandible joint opening apart with a predetermined and repeatable magnitude of force, wherein said predetermined and repeatable force is equal to said "end-feel" force;
   continuously measuring the maximum extension of said apparatus within said mandible joint opening;
   determining when said predetermined and repeatable force has been achieved, so that said continuous measurement of said mandible joint opening provides said border position.

18. The method of claim 17 wherein said step of forcing said mandible joint opening apart comprises the steps of moving an upper jaw piece in contact with an upper jaw of said patient away from a lower jaw piece in contact with a lower jaw of said patient, and
   wherein said step of determining said predetermined force comprises the step of applying a predetermined force against said lower jaw piece to move said lower jaw piece away from said upper jaw piece as measured by predetermined degree of compression of a spring.

19. The method of claim 17 wherein said step of forcing apart said mandible joint opening comprises the step of forcing an upper jaw piece in contact with upper jaw of said patient away from a lower jaw piece in contact with a lower jaw of said patient, and
   wherein said step of determining when said predetermined force has been achieved comprises the step of activating a release mechanism which releases one of said upper and lower jaw pieces when said predetermined force as applied to said selected one of said jaw pieces has been exceeded.

20. The method of claim 19 wherein said step of releasing comprises the step of activating a detent mechanism coupling said selected one of said jaw pieces to said apparatus.

21. The method of claim 17 wherein said step of forcing said mandible joint open comprises providing said predetermined force at an arbitrary user-selected rate of change.

* * * * *